US005589389A

United States Patent [19]
Pages et al.

[11] Patent Number: 5,589,389
[45] Date of Patent: Dec. 31, 1996

[54] APPARATUS FOR CAUSING MEDICINAL PRODUCTS TO PENETRATE INTO RED BLOOD CELLS

[75] Inventors: Etienne Pages; Claude Ropars, both of Saint-Avertin; Christophe Bailleul, Montfermeil, all of France

[73] Assignee: Fondation Nationale de Transfusion Sanguine, Paris Cedex, France

[21] Appl. No.: 170,352

[22] PCT Filed: Jul. 2, 1992

[86] PCT No.: PCT/FR92/00623

§ 371 Date: Jan. 3, 1994

§ 102(e) Date: Jan. 3, 1994

[87] PCT Pub. No.: WO93/00940

PCT Pub. Date: Jan. 21, 1993

[30] Foreign Application Priority Data

Jul. 3, 1991 [FR] France ................................. 91 08302

[51] Int. Cl.[6] .............................. C12M 1/12; C12M 3/06
[52] U.S. Cl. ........................ 435/306.1; 435/2; 435/297.2
[58] Field of Search ........................... 435/2, 172.1, 287, 435/311, 316, 283.1, 285.1, 297.1, 297.2, 306.1; 935/85; 604/4–6, 408–410; 422/44–48; 210/645, 647, 321.72, 321.75, 321.78, 321.8, 321.84, 321.87, 321.89

[56] References Cited

U.S. PATENT DOCUMENTS 3,399,536  9/1968  Walz .
3,839,204  10/1974  Ingenito et al. ........................... 422/46
3,853,479  12/1974  Talonn et al. ............................. 422/46
4,327,710  5/1982  DeLoach et al. .
4,517,080  5/1985  DeLoach et al. .......................... 210/85
4,652,449  3/1987  Ropars et al. ........................... 424/101
4,668,214  5/1987  Reeder .
4,752,586  6/1988  Ropars et al. ........................... 435/287

FOREIGN PATENT DOCUMENTS 0292076  11/1988  European Pat. Off. .
2529463  1/1984  France .

Primary Examiner—William Beisner
Attorney, Agent, or Firm—Foley & Lardner

[57] ABSTRACT

An apparatus for incorporating one or more biologically active substances into red blood corpuscles (erythrocytes) by lysis and resealing technique comprises a washing unit, a lysis unit and a resealing unit. The washing unit obtains a suspension of erythrocytes from complete or incomplete blood. The lysis unit cools the erythrocyte suspension to a temperature below 10° C. and maintains this temperature while the suspension is processed through a dialysis unit and subsequently exposed to the active substance. The treated erythrocyte suspension is held in a retardation pouch for a predetermined time and thereafter fed to the resealing unit, which heats the treated suspension to a temperature higher than 20° C. and maintains this temperature while the treated suspension is exposed to the resealing product. The suspension exposed to the resealing product is collected in a collecting pouch for a predetermine period before it is discharged to the washing unit.

20 Claims, 2 Drawing Sheets

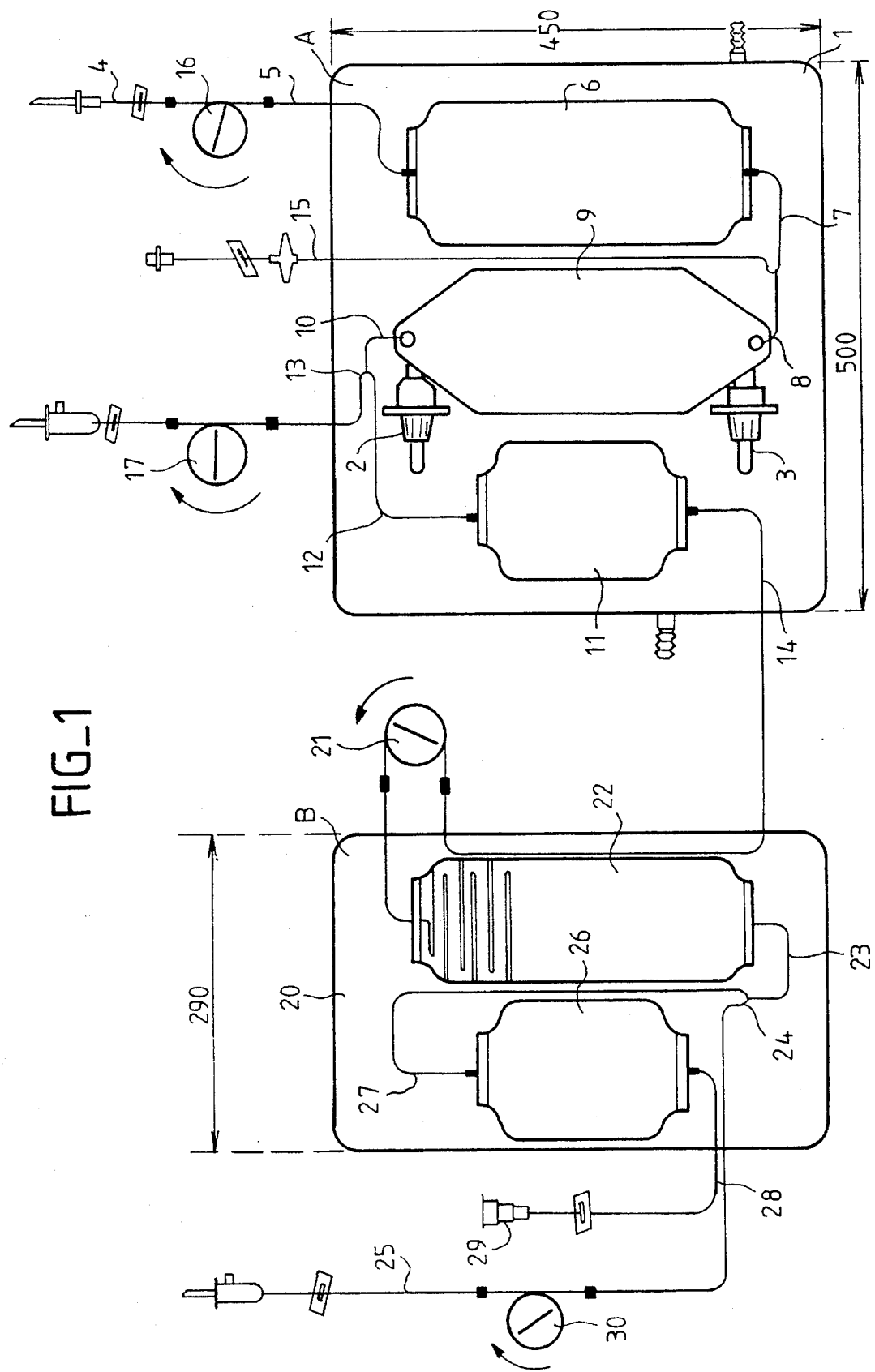
FIG_1

FIG_2
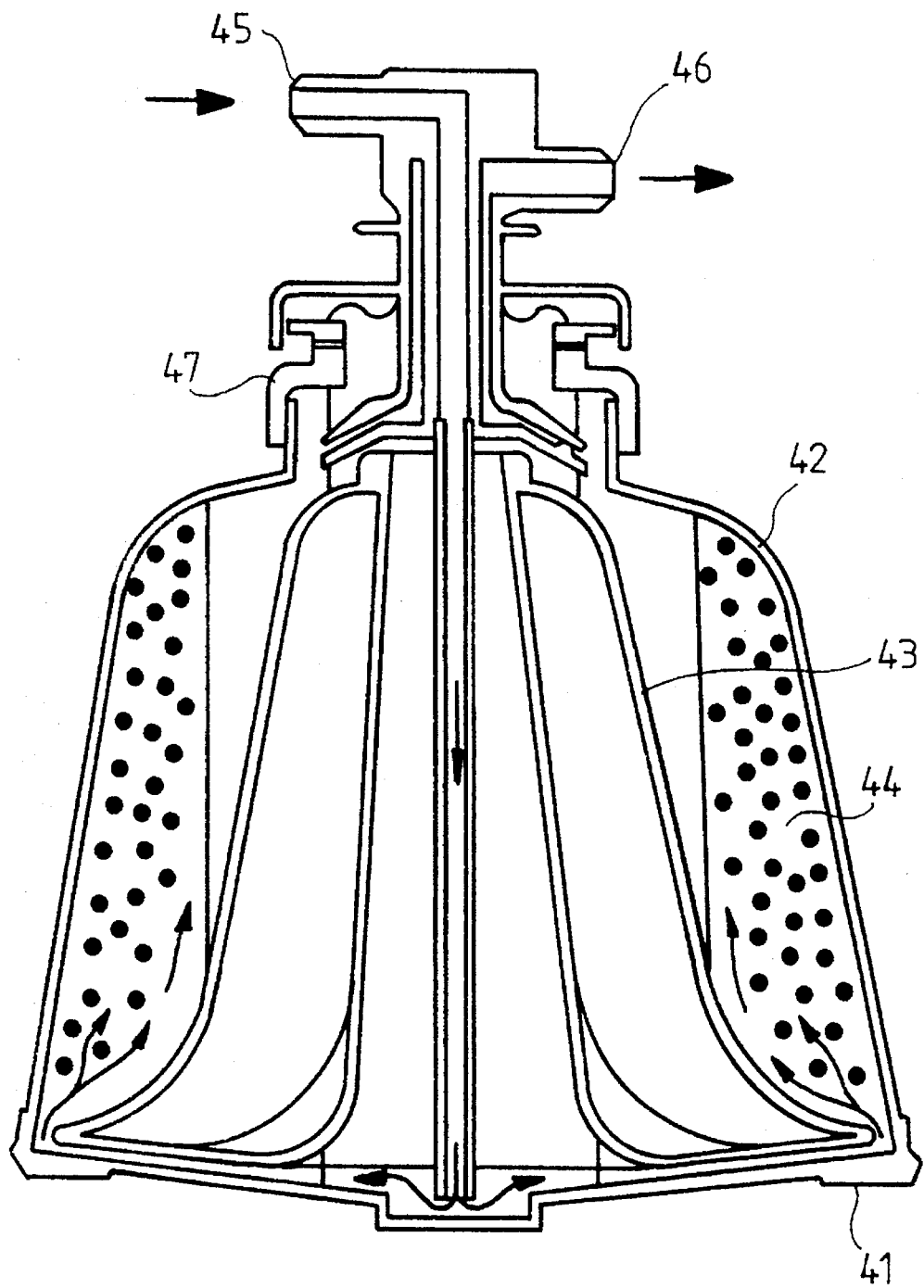

APPARATUS FOR CAUSING MEDICINAL PRODUCTS TO PENETRATE INTO RED BLOOD CELLS

BACKGROUND

The present invention relates to a device permitting the implementation of the so-called "lysis-resealing" technique which makes it possible to incorporate active ingredients into red blood cells.

The lysis-resealing technique is described in patents EP 101341, U.S. Pat. Nos. 4,752,586 and 4,652,449, and its principle will not be redescribed in detail.

In the so-called "lysis-resealing" technique, the primary compartment of a first dialysis element is continuously supplied with an aqueous suspension of erythrocytes, the secondary compartment containing an aqueous solution which is hypotonic relative to the suspension of erythrocytes in order to lyse the erythrocytes. The erythrocyte lysate is then in contact with the substance exhibiting a biological activity and in order to reseal the erythrocyte membrane, the osmotic and/or oncotic pressure of the erythrocytic lysate is increased after bringing it into contact with the biologically active substance.

In this preferred embodiment of this process, the resealing is performed in a separate vessel although it is possible, as described in the patent, to carry out the resealing using successively two dialysis bobbins.

More specifically, in this type of process, the globular pellet is obtained by centrifugation and decantation of plasma, which is kept at 4° C. for the treatment. The red blood cells are subjected to a first series of washes. The first wash in physiological saline makes it possible to obtain a globular concentrate whose buffy coat (white blood cells, platelets) is removed. The concentrate of red blood cells is then brought into contact with IHP (inositol hexaphosphate) for example during the subsequent two washes.

In hypotonic medium, the red blood cell swells up to a volume which may be equal to 175% of its initial value (ROPARS et al., 1986). It is at this stage that pores of a few hundred angstroms appear. There is then exchange between the extracellular and intracellular media especially for the substance to be internalized. After addition of a hypertonic solution to the hemolysate, the isotonicity is restored, the pores become closed again and entrap the IHP for example inside the red blood cell. An incubation phase, which is necessary for the charged red blood cells to recover permeability characteristics identical to those of the initial red blood cells, follows in regenerating solution. After resealing, the red blood cells are subjected to a second series of washes. The first two washes use a solution of physiological saline: they make it possible to remove the non-resealed red blood cells.

The red blood cells are then resuspended in autologous plasma to a physiological hematocrit which permits transfusion. The converted unit of blood consists of red blood cells with improved oxygen binding and transporting properties whose morphological and physiological characteristics are similar to unconverted red blood cells.

The implementation of the lysis-resealing process permits the incorporation of a large number of active ingredients into red blood cells, which red blood cells can be reinjected into the same patient or into different patients. For example, the incorporation of IHP into the erythrocytes makes it possible to modify the affinity constant of hemoglobin for oxygen.

Other applications of this process are described in the patents mentioned above.

SUMMARY

The present invention relates to a device intended to allow the incorporation of one or more biologically active substances into red blood cells by the lysis-resealing technique. It comprises a washing unit which permits, starting with a blood, whole or otherwise, a suspension of red blood corpuscles to be obtained; and a lysis and resealing unit consisting of a lysis module at a temperature less than 10° C. and a resealing module at a temperature greater than 20° C., all the elements of the lysis and resealing unit entering into contact with the suspension of erythrocytes being designed for a single use.

"Designed for a single use" should be understood to mean that even when the elements are intended to be reused, they will be reused only after sterilization and/or viral inactivation but will be designed as elements for single use, that is to say capable of being easily assembled and dismantled and of low cost.

In the device of the present invention, the lysis module A comprises a set ensuring the transport of a lysis buffer (2) up to the inlet of the dialysis cartridge and the optional discharge (3) of the said lysis buffer, as well as the elements which make it possible to maintain the module at a determined temperature, especially 4° C., a removable set preferably for single use, incorporating a dialysis cartridge (9) capable of being attached to the lysis buffer feed in order to supply one of the compartments, the other compartment of the cartridge being connected at the venous end to a vessel (6) intended for adjusting the temperature of the erythrocyte suspension, and at the arterial end to a storage vessel (11).

The resealing module comprises a set of elements which allow the module to be maintained at a determined temperature, preferably 37° C., and a removable set, preferably for single use and incorporating from upstream to downstream, a vessel (22) intended to ensure adjustment of the temperature of the suspension, connected to a vessel (26) incorporating an access for resealing solution (28).

These modules as a whole incorporate a pump which permits the entry of the erythrocyte suspension into the lysis module, a pump which permits the exit of the erythrocyte suspension from the resealing module, and an intermediate pump ensuring the circulation between the lysis module and the resealing module. These pumps are preferably peristaltic pumps, which avoid all contact with the suspension.

The device preferably incorporates, in addition, before the resealing unit, a small tube for admitting a solution of an active ingredient to be internalized, for example ATP (adenosine triphosphate). For the internalization, depending on the substance to be internalized, the latter may be introduced with the erythrocyte suspension before the lysis (case of IHP), or alternatively added after the lysis at 4° C. (case of ATP). The vessels intended to ensure the adjustment of the temperature of the suspensions are preferably plastic pouches incorporating internal baffles. These preferably elongated pouches are placed vertically and supplied via the top and discharged via the bottom.

The heating and cooling of the modules can be ensured by a support plate which will receive, on one face, the elements for single use and the other face will be in contact with a cooling or heating element. Likewise, in the case of the lysis module, the lysis buffer will be cooled by passage into an appropriate cooling system.

The dialyzer itself can be used as heat exchanger between the blood and the lysis buffer which pass through it, without resorting to other artifices. These heat exchanges permit a specific treatment of the red blood corpuscles.

The various modules placed on these plates, whose form will be preferably adapted in order to attach the removable elements, will be able to receive a cover and a coating which will ensure that the temperatures are preferably maintained at 4° C. and 37° C.

The washing element may take various forms; it will be preferably of the separating bowl type, it will also be possible to reuse it to perform a washing after treatment of the suspension.

The washing element is, in its principle, a reservoir having a rotational symmetry and comprises two casings in the form of concentric truncated cones, the separating chamber itself being the space between the two conical surfaces.

One of the characteristic features of the separating bowl is that its filling is performed at its base and at its periphery; any product introduced, if it is less dense than those already present in the separating chamber will therefore have to circulate in the direction opposite to sedimentation.

The components separated from the product introduced become organized in concentric rings and become concentrated through the gradual decrease in their diameter and the decrease in their height by the conicity of the separating chamber.

The various fluids circulate and make their way towards this bowl by virtue of a peristaltic pump and eight pneumatic clamps. An air detector, two optical sensors and two coder wheels placed, one over the axis of the pump, and the other over the axis of the centrifuge, permit the collection of information necessary for the management of the peripheral units as a whole which are the pump, the centrifuge and the clamps.

Elements with the same type of functions are already commercialized especially by the company Haemonetics on the machines V50/PCS/CELL SAVER®, for example the washer COBE 2997, the separators COBE Spectra, DIDECO Vivacell, BAXTER CS 3000 and Autopheresis PC.

The description below represents an embodiment of the device according to the invention, using preferably a separator from the company Haemonetics V50®.

BRIEF DESCRIPTION OF THE DRAWINGS

FIG. 1 is a general schematic representation of the device for single use.

FIG. 2 is a schematic representation of the separating bowl.

DETAILED DESCRIPTION

The lysis-resealing device represented in FIG. 1 incorporates a lysis unit A and a resealing unit B.

The lysis unit A comprises of an evaporator which is in contact with a stainless steel metal plate (1) having the form of the elements of the kit for single use. The other side of the evaporator (not represented) is in contact with the non-disposable heat exchanger containing metal coil. In operation, a second metal plate which is cooled or alternatively simply made from insulating material joined to the first encloses the kit for single use in a minimum cooled volume. This box thus constituted dictates, in addition, the maximum volume of the various pouches and small tubes.

This metal plate (1) incorporates two elements permitting the arrival (2) and departure (3) of the lysis buffer, of which the supply system is not represented, but consists essentially of a pump, a cooling circuit and a supply tank. On the plate (1) is removably attached the part of this lysis module called kit for single use. This part is composed, from the blood inlet to the outlet of the blood treated: of a perforator (4) followed by a small PVC tube (5) which opens out into a special pouch welded in the form of a coil (6) and acting as heat exchanger; a 1 to 1.5 m coil made from a Stainless Steel tube ⅛ OD could be used in place of the coil-shaped PVC pouch for the heat exchanges with the blood. The other end of this exchanger is itself linked to a small tube (7) which is connected via a special male luer to the arterial inlet (8) of the dialysis cartridge (9). At the venous outlet (10) of the dialyzer, a small tube (12) leads to the top of a 600 ml PVC pouch (11) which serves as buffer volume, this small tube is joined by another to form a "Y" (13), between the outlet of the dialyzer (10) and the "retardation" pouch (11). Finally, a last small tube (14) leads from the bottom of this pouch to the outlet of the module. The lysis buffer inlet of the dialyzer comprises a small tube passing across a peristaltic pump and leading to an exchanger formed by a non-disposable metal coil mounted on the evaporator. The outlet of the dialyzer, as regards the dialysis liquid, is for its part a simple small tube opening out into a reservoir. The elements to be cooled are therefore overall of two types, on the one hand the kit for single use made from plastic material (PVC, polycarbonate) and the reusable metal kit both in intimate contact with the thermoregulated metal plate, and on the other hand the fluids (blood, lysis buffer, solution of active ingredient) which circulate and are held in the kit in whose contact acquire the desired temperature.

The lysis module also comprises a pump small tube (15) for additive solution which can be mixed with the blood lysed at 4° C., for example ATP or a small molecule. This small tube is linked to the small tube (7). Two levels are therefore possible for bringing the active substance and the red blood cells into contact, before and immediately after the lysis.

Finally, the blood circulation is ensured by a peristaltic pump (16) which is directed by a set of controls like the other peristaltic pumps of the device. The pump (17) fitted onto the small tube (18) is linked to the "Y" (13) and is essentially intended to ensure the purge of the dialysis bobbin (9). This pump (17), like the previous one, is directed by the central control unit.

The delivery of active ingredient by the small tube (15) can be achieved either manually, or via a pump (not represented).

The resealing module B is itself also made up of a metal box (20) provided with a port (not represented) which closes over a kit for single use. This metal box, upon contact with a heat source, will ensure that the module in question is maintained at 37°. The kit for single use is composed, from the inlet for the blood at 4 degrees to the outlet of the heated blood, of a small tube (14) coming directly from the "4 degrees" module, and which permits preheating of the blood. This small tube temporarily leaves the module and passes into the body of a blood pump (21) before joining a heat exchanger (22) identical to that used in the 4 degrees module. The small tube (23) which leaves the exchanger, placed for its part in the 37 degrees module, joins a "Y" (24) one of whose branches ends with a male perforator (25) (to be connected to the resealing bottle). The other branch of the "Y" leads to 600 ml PVC pouch (26). This pouch has two opposite small tubes for access (27 and 28), permitting the first blood to enter to be also the first to leave, and is identical to the "retardation" pouch of the "4 degrees" module. A small tube ending with a female mouthpiece (29) for the perforator constitutes the outlet of this "retardation" pouch.

Finally, the admission of the resealing solution which is achieved via the small tube (25) and the pump (30) is also controlled like the previous peristaltic pumps at the central control unit. As can be observed on reading this figure, the set of small tubes for the four pouches (6), (11), (22), and (26) and the dialysis bobbin (9), which are the elements in contact with the suspension of red blood cells, are removably placed in the two resealing units, and can consequently either be resterilized or alternatively discarded after use.

The pouches for adjusting the temperature are made from PVC and comprises two practically rectangular and identical PVC sheets welded together in the form of a coil. This coil leads from a small PVC tube (5) situated at the top of the pouch, to a second tube (7), which is welded to the bottom of the pouch.

Inside the closed box in which the pouch is enclosed, the maximum distance between the inner faces of the pouch will be fixed and of the order of few tens of mm. In this manner, the exchanger volume will be small (from 10 to 20 ml) and the surface in contact with the plate (1) at 4 degrees will be maximum.

The dialysis cartridge (9) incorporates a parallelepipedic box made from rigid plastic material. This box is separated into two compartments by semi-permeable membranes, each of these compartments has two inlet-outlet tubes. One of the compartments is crossed by blood, the other by lysis buffer. The assembling of this element in the module is performed such that blood circulates from the bottom to the top so as to ensure a natural purge of the blood compartment.

The dialysis cartridge may also be of the "hollow fiber" type, where the two compartments comprises, for the blood compartment, the inside of the hollow fibers (made from semipermeable materials) and for the lysis buffer compartment, the volume outside the fibers and inside the rigid box enclosing these fibers.

The dialysis outlet buffer pouch (11) is a transfer pouch with a maximum volume of 600 ml, enclosed in a volume of about 500 ml in which it increases in volume during its filling. It has the special feature that the small tube for supplying and that for discharging are both mounted on a short side of the pouch, but in an opposite manner. For a vertical position of the pouch, the first blood to enter (via the top) will also be the first to leave (via the bottom).

FIG. 2 represents the section of the washing unit, the description of this separation bowl will not be made in detail since it is a product which can be found on the market and which was adapted for the present use.

In the sectional view of FIG. 2, it can be seen that the separating bowl (41), in its principle, consists of two rigid casings in the form of concentric truncated cones (42) and (43). The first is external (42) and the second (43) is placed on the same axis and included in the first. The separating chamber (44) is the space between the two conical surfaces. This bowl is provided with an injecting system (45) and a collecting system (46), separated from the separating chamber by a rotating joint (47) at the vertex of the two truncated cones.

The reservoir, during the separation of the cells from the introduced suspension, is set into rotation by a centrifuge, the injecting and collecting system is for its part maintained by two articulated arms in the closed position.

The injector (45), via its connection to a network of small tubes, permits the introduction, into the separator (44), of the cell suspension to be separated, or, during stoppage of the bowl, the emptying thereof.

The collector (46), as for its part, permits the collection of the separated constituents, which are presented to it sequentially, pushed outwards by the introduced suspension. The collector too is connected to a network, which amounts to a small tube which joins a waste pouch.

The solid elements of the suspension are gradually concentrated by centrifugation towards the outside of the chamber (44). A detection system, previously calibrated before the centrifugation, makes it possible, when the concentration of red blood cells has reached a determined volume, and/or when the red blood cells have been appropriately washed, to obtain a suspension of red blood cells having the desired characteristics.

The examples below are intended to demonstrate other advantages and characteristics of the present invention, but do not limit it in any manner.

EXAMPLE I

Separation of Red Blood Corpuscles from Plasma

The separation of red blood corpuscles is performed during the first wash, called wash I, and permits the treatment of the blood, before the step of reversible lysis of the red blood corpuscles and their resealing.

The wash I, performed on a unit of whole blood, comprises the following steps:
removal of plasma,
removal of leucocytes
removal of platelets
adjustment of the hematocrit
suspension of the red blood corpuscles in a solution of product to be internalized (IHP).
control of the osmolarity.

These operations which are currently manual, are performed automatically by virtue of the present invention. When a large quantity of blood needs to be treated, this wash may comprise several cycles.

Sequence of Operations

A cellular suspension of about 40% hematocrit is prepared by addition of physiological saline from an erythrocytic concentrate, this being automatically and simultaneously to the introduction of the erythrocytic concentrate into the bowl, by alternating a quantity of water and blood in a proportion which is calculated by the machine so as to obtain 40% hematocrit.

The diluted pellet is introduced into the bowl described in FIG. 2 until optical detection or vacuity of the pouch is achieved, a volume of about 480 cc, at an output of the blood pump of 100 cc/min (adjustable from 0 to 250 ml/min) and a centrifuge rotation speed of 6000 rpm. The supernatant solution is collected in a 5 liter waste pouch. It is during this step that the hematocrit is empirically determined by stoppage of the filling of the separator at a determined supernatant/cell interface level (42 ml), this under precise output and centrifugation conditions.

The washing of the red blood corpuscles is performed by introduction into the bowl of a programmed volume of 9% NaCl solution, this at a variable output, under the control of the optic of the small tube. The output of the pump is controlled in such a manner that the liquid leaving the bowl is at a hematocrit of the order of 1%, allowing the removal of the buffy coat while minimizing the loss of red blood cells. This step relates to the completion of the plasma removal, as well as the removal of the platelets and the white blood cells.

The blood now being in the form of a suspension of "pure" red blood cells in the washing solution, the suspension in IHP solution is achieved by repetition (four times) of the following procedure:

a small volume of IHP is introduced into the bowl (of the order of 50 ml to 38 mM/l of IHP), which displaces the washing solution towards the waste pouch, then the centrifuge is stopped so as to homogenize the IHP in the solution of suspension of red blood cells, immediately followed by restarting of the centrifuge and a waiting period of about one minute in order to obtain correct sedimentation.

When the number of desired washes is achieved, the emptying of the bowl into a transfer pouch (150 ml/min) can then take place.

In the case of the volume of blood to be treated is not sufficient to obtain a hematocrit of 72% before the removal of leucocytes in the separator (265 cc bowl) that is to say if the volume of red blood corpuscles is less than 191 ml, the machine will alarm (detection of air). The user will have in this situation the choice between 3 alternatives:
continue the washing with an abnormal hematocrit
connect another unit and continue the filling of the bowl normally
if no other blood apart from that already in IHP is available, the latter is used to complete the filling of the bowl to 72% hematocrit. The washing can then be completed as described above.

The wash I is then finished and the dialysis phase can start.

EXAMPLE II

Lysis and Resealing Step

This lysis and resealing phase occurs after the wash I and therefore involves a suspension of red blood corpuscles (70%) in an IHP solution of variable volume, of 265 cc minimum to about 1.3 liters. This suspension will be subjected to the following operations:
reduction of the temperature to 4° C.
passage into the dialyzer
mixing with an ATP solution
waiting at 4 degrees for about 10 minutes
heating to 37° C.
mixing with the resealing solution
waiting for the wash II at 37° C. for about 30 minutes.

Sequence of Operations

The suspension of red blood corpuscles coming from the wash I is carried by a peristaltic pump (16) through a heat exchanger (6) where its temperature decreases to 4° C. This output is adjustable from 0 to 32 cc/min in steps of 1 ml/min, and determines the blood transit time in the dialyzer (9) for a given dead volume of the blood compartment. The temperature, for its part, is adjustable from 1° C. to room temperature. This pumping operation is carried out in an uninterrupted manner until the pump inlet air detector is activated, indicating the vacuity of the pouch of blood to be treated. As this very moment, and in order to allow the emptying, even partial, of the heat exchanger, then of the dialysis cartridge, sterile air will be pumped for a fixed volume.

The red blood cells, once cooled in the heat exchanger (in suspension in the IHP solution) cross the blood compartment of a dialyzer at the output dictated by the user's program. The temperature of the dialyzer is controlled (4° C.). The transmembrane pressure is measured. The output of the lysis buffer pump (not represented) is regulated so as to maintain the transmembrane pressure constant and at the desired level, from 0 to 300 mmHg. The lysis buffer is itself maintained at 4° C. by passage through a nondisposable heat exchanger.

At the outlet of the dialyzer, and still at 4° C., the cellular suspension obtained is proportionally mixed by means of the small tube (17) with an ATP solution, adjustable from $\frac{1}{20}$th to $\frac{1}{5}$th (ratio preadjusted to $\frac{1}{10}$th), then allowed to stand for a maximum of 15 minutes, (period adjustable from 0 to 20 min) in the pouch (11). The pump (17) is charged with the transport of the ATP solution, its output range extends from 0 to 16 ml/min. After that, the suspension is pumped at an adjustable output of 0 to 32 ml/min in steps of 1 ml/min, and heated to 37° C. by passage through a heat exchanger. This is accomplished by the pump (21) situated after the exchanger, so as to work on a portion of small tube which is not rigidified by a too low temperature. Then proportionally to the blood output and in a ratio of $\frac{1}{5}$th to $\frac{1}{20}$th, the resealing product is mixed in the pouch (26) with the blood heated to 37 degrees after passage through the heating pouch (22). A peristaltic pump (21) is used for this purpose, its output range extending from 0 to 16 ml/min.

The final step is a waiting phase for the product obtained in order to obtain the complete resealing of the red blood corpuscles. The suspension of red blood corpuscles is maintained for 15 to 30 min at the temperature of 37° C. in the pouch of about 600 ml (26). After that, the wash II can then be performed.

EXAMPLE III

Washing of the Red Blood Corpuscles After Resealing

The object of the second wash is to wash and resuspend, in plasma, the cellular suspension obtained after the lysis and resealing phase. It comprises the following steps:
filling the bowl and removing the solution, resuspending the red blood corpuscles, this solution containing essentially IHP, ATP and free hemoglobin.
removal of the stromata of cells.
suspension of the treated red blood corpuscles in a preserving solution, plasma or a solution of synthetic macromolecules.

Sequence of Operations

The suspension of cells treated by dialysis is introduced into the bowl already used for the wash I at a rate of 100 cc/min, diluted with physiological saline in a ratio of 1:2 and a centrifuge rotation speed of 5000 rpm. This phase is stopped after a volume of about 1 l has been introduced, or a detection of air in the small tube for supplying the bowl has occurred, an indication of the vacuity of the pouch. In the case of a detection of air, the question arises as to whether to start the washing or to wait for the availability of other blood to be washed.

The wash may then begin with the introduction, into the bowl, of a programmed volume of 9% NaCl solution, at a variable rate and for a centrifugation speed of 6000 rpm, under the control of the optic of the small tube. The output of the pump is controlled such that the liquid leaving the bowl is at a maximum hematocrit of the order of 1%, permitting the removal of stromata of cells while minimizing the loss of red blood cells. This phase removes a portion of the free hemoglobin without, however, that which is present in the red blood corpuscles being actually affected.

The centrifuge is then stopped, then immediately restarted, so as to homogenize the solution of suspension of red blood cells., before restarting, for a determined volume, the introduction of physiological saline. Three steps of washing with 500 ml of physiological saline are thus performed.

This centrifuge stop and restart phase is repeated a second time, but only for two steps of about 100 ml, the physiological saline being replaced with plasma.

The centrifuge is then stopped and the bowl is emptied into a transfer pouch at a rate of 150 ml/min.

The washes I and II may correspond to a sequence of cycles (one or more), a cycle corresponding to a set of phases and steps.

We claim:

1. An apparatus for introducing at least one biologically active substance into erythrocytes, comprising:

a settling bowl for removing plasma, leucocytes, platelets of blood, and adjusting hematocrit and controlling osmolarity of blood, and for obtaining erythrocytes suspended in a solution of a product to be internalized;

a lysis unit for cooling the erythrocyte suspension obtained from the settling bowl and introducing the active substance into the cooled erythrocyte suspension, the lysis unit having cooling means for maintaining the erythrocyte suspension at a temperature less than 10° C., a dialysis cartridge for receiving the cooled erythrocyte suspension and a first collection pouch for receiving the erythrocyte suspension processed by the dialysis cartridge, and means for introducing the active substance into the first pouch along with the processed erythrocyte suspension; and a resealing unit for heating the erythrocyte suspension treated with the active substance from the first pouch and introducing a resealing product into the heated and treated erythrocyte suspension, the resealing unit having heating means for maintaining the temperature of the treated erythrocyte suspension greater than 20° C., a second collection pouch for receiving and holding the heated and treated erythrocyte suspension, and means for introducing the resealing product into the second pouch along with the heated and treated erythrocyte suspension.

2. An apparatus according to claim 1, wherein the lysis unit further comprises means for introducing and discharging a lysis buffer to and from the dialysis cartridge, where the cooling means in the lysis unit maintains the temperature of the erythrocyte suspension at 4° C.

3. An apparatus according to claim 2, wherein the dialysis cartridge has two compartments separated by at least one semipermeable membrane, the lysis buffer being introduced into one of the compartments and the erythrocyte suspension being introduced into the other compartment.

4. An apparatus according to claim 2, wherein the lysis unit further includes means for cooling the lysis buffer before the lysis buffer is introduced into the dialysis cartridge.

5. An apparatus according to claim 1, wherein the heating means in the resealing unit maintains the temperature of the treated erythrocyte suspension at 37° C.

6. An apparatus according to claim 1, further comprising a peristaltic pump for transporting the treated erythrocytes from the first pouch to the resealing unit.

7. An apparatus according to claim 1, further comprising a first peristaltic pump for introducing the erythrocyte suspension into the lysis unit and a second peristaltic pump for withdrawing the treated erythrocyte suspension from the resealing unit.

8. An apparatus according to claim 1, wherein the first and second pouches are made from plastic material.

9. An apparatus according to claim 1, wherein the lysis unit further includes a baffled cooling pouch for receiving the erythrocyte suspension from the settling bowl, wherein the cooling pouch feeds the cooled erythrocyte suspension to the dialysis cartridge and wherein the resealing unit further includes a baffled heating pouch for receiving the treated erythrocyte suspension from the first pouch, wherein the heating pouch feeds the heated and treated erythrocyte suspension to the second pouch.

10. An apparatus according to claim 1, wherein the first and second pouches are vertically situated and the erythrocyte suspension is introduced from the top and discharged from the bottom.

11. An apparatus according to claim 1, wherein the dialysis cartridge is vertically situated and the cooled erythrocyte suspension is introduced from the bottom and the processed erythrocyte is discharged from the top.

12. An apparatus according to claim 1, further comprising means for receiving and washing the heated and treated erythrocyte suspension from the second pouch.

13. An apparatus according to claim 12, wherein the washing means is the settling bowl.

14. An apparatus according to claim 1, wherein the lysis unit further includes means for introducing another product into the dialysis cartridge.

15. An apparatus according to claim 1, further including means for purging the lysis unit or the resealing unit or both.

16. An apparatus according to claim 1, wherein the lysis unit and the resealing unit are thermally insulated.

17. An apparatus according to claim 1, wherein the heating and cooling means each comprise a thermally conductive plate having a respective heating or cooling circuit on one side in contact therewith, wherein at least the dialysis cartridge and the first and second collection pouches of the lysis unit and the resealing unit are removably attached to the opposite sides of the plates.

18. An apparatus for introducing at least one biologically active substances into erythrocytes suspended in a solution of a product to be internalized, comprising:

a) a lysis unit comprising:
      a cooling heat exchanger having an inlet for receiving the erythrocyte suspension and an outlet for outputting the erythrocyte suspension at a temperature of about 4° C.;
      a dialysis cartridge having an inlet for receiving the cooled erythrocyte suspension from the cooling heat exchanger and an outlet for outputting the erythrocyte suspension processed by the dialysis cartridge;
      means for introducing and discharging a lysis buffer solution into and out of the dialysis cartridge;

a retardation pouch having an inlet and an outlet, wherein the processed erythrocyte suspension from the dialysis cartridge is collected in the retardation pouch;

means for introducing the active substance into the retardation pouch along with the processed erythrocyte suspension; and means for maintaining the temperature of the erythrocytes in the dialysis cartridge and the retardation pouch at about 4° C.; and b) a resealing unit comprising:

a heating heat exchanger having an inlet for receiving the treated erythrocyte solution from the retardation pouch and an outlet for outputting the treated erythrocyte suspension at a temperature of about 37° C.;

a collection pouch having an inlet and an outlet, wherein the heated and treated erythrocyte suspension from the heating heat exchanger is collected in the collection pouch;

means for introducing a resealing product into the collection pouch along with the heated and treated erythrocyte suspension; and means for maintaining the temperature of the erythrocyte suspension in the collection pouch at about 37° C.

19. An apparatus according to claim 18, wherein the cooling heat exchanger comprises a baffled cooling pouch for receiving the erythrocyte suspension, wherein the cooling pouch feeds the cooled erythrocyte suspension to the dialysis cartridge and wherein the heating heat exchanger comprises a baffled heating pouch for receiving the treated erythrocyte suspension from the retardation pouch, wherein the heating pouch feeds the heated and treated erythrocyte suspension to the collection pouch.

20. An apparatus according to claim 19, wherein the lysis unit further includes means for cooling the lysis buffer before the lysis buffer is introduced into the dialysis cartridge.

* * * * *